United States Patent
Pilkington et al.

(10) Patent No.: US 10,410,305 B1
(45) Date of Patent: Sep. 10, 2019

(54) EXCEPTION-BASED INTEGRATED PATIENT ACCESS WORKFLOW

(71) Applicant: Experian Health, Inc., Franklin, TN (US)

(72) Inventors: Edmond Chase Pilkington, Rockvale, TN (US); Joseph M. Magee, III, Drexel Hill, PA (US); Howard Bright, Kingston Springs, TN (US); Michael Moreau, Nashville, TN (US); Lance Mansfield, Seattle, WA (US); Marcus Padgett, Villa Park, IL (US)

(73) Assignee: EXPERIAN HEALTH, INC., Franklin, TN (US)

( * ) Notice: Subject to any disclaimer, the term of this patent is extended or adjusted under 35 U.S.C. 154(b) by 0 days.

(21) Appl. No.: 13/770,587

(22) Filed: Feb. 19, 2013

Related U.S. Application Data

(60) Provisional application No. 61/600,600, filed on Feb. 18, 2012, provisional application No. 61/765,317, filed on Feb. 15, 2013.

(51) Int. Cl.
*G06Q 50/22* (2018.01)

(52) U.S. Cl.
CPC .................... *G06Q 50/22* (2013.01)

(58) Field of Classification Search
CPC ....... G06Q 50/22–50/24; G06F 19/322; G16H 10/00
See application file for complete search history.

(56) References Cited

U.S. PATENT DOCUMENTS

| | | | |
|---|---|---|---|
| 7,606,721 B1 | 10/2009 | Donnelly et al. | |
| 8,688,480 B1 | 4/2014 | Singh et al. | |
| 10,354,211 B1 | 7/2019 | Pilkington | |
| 2002/0026328 A1 | 2/2002 | Westerkamp et al. | |
| 2003/0140044 A1* | 7/2003 | Mok et al. | 707/10 |
| 2004/0230458 A1* | 11/2004 | Takayama et al. | 705/3 |
| 2004/0244005 A1 | 12/2004 | Ancier | |
| 2005/0273363 A1* | 12/2005 | Lipscher et al. | 705/2 |
| 2006/0129435 A1* | 6/2006 | Smitherman et al. | 705/3 |
| 2007/0022086 A1* | 1/2007 | Elsholz | 707/1 |

(Continued)

OTHER PUBLICATIONS

Office Action dated Mar. 7, 2016, in co-pending U.S. Appl. No. 13/770,660, 29 pgs.

(Continued)

*Primary Examiner* — Sheetal R Paulson
(74) *Attorney, Agent, or Firm* — Merchant & Gould

(57) ABSTRACT

An exception-based integrated patient access workflow via a single user interface is provided. When patient data associated with a healthcare encounter is received, various rules may be applied to cross-check the received data with other stored and received data to ensure correct patient data and to ensure accurate information for downstream patient access workflow processes. An indication of discrepant data, missing data, or input/user-interaction that may be needed for performance of a patient access workflow process may be provided. The indication may be provided via alerts displayed in an integrated user interface. Accordingly, a user may be able to address and resolve alerts to ensure patient access workflow processes are performed prior to a healthcare encounter.

16 Claims, 16 Drawing Sheets

(56) References Cited

U.S. PATENT DOCUMENTS

| | | | |
|---|---|---|---|
| 2007/0027714 A1* | 2/2007 | Fenno | G06F 19/327 |
| | | | 705/2 |
| 2008/0027965 A1 | 1/2008 | Garrett et al. | |
| 2009/0216562 A1* | 8/2009 | Faulkner et al. | 705/3 |
| 2011/0029330 A1 | 2/2011 | Paddock, III et al. | |
| 2013/0046558 A1* | 2/2013 | Landi et al. | 705/3 |
| 2013/0046560 A1* | 2/2013 | Theus | G06Q 10/10 |
| | | | 705/4 |

OTHER PUBLICATIONS

Edmond Chase Pilkington et al., U.S. Appl. No. 13/770,660, Account Prioritazation for Patient Access Workflow, filed Feb. 19, 2013.

Office Action dated Oct. 22, 2014, in co-pending U.S. Appl. No. 13/770,660, 20 pgs.

Office Action dated Oct. 21, 2015, in co-pending U.S. Appl. No. 13/770,660, 26 pgs.

Office Action dated Feb. 3, 2017, in co-pending U.S. Appl. No. 13/770,660, 36 pgs.

Office Action dated Jul. 12, 2017, in co-pending U.S. Appl. No. 13/770,660, 19 pgs.

Office Action dated Feb. 12, 2018, in co-pending U.S. Appl. No. 13/770,660, 17 pgs.

Office Action dated Aug. 23, 2018, in co-pending U.S. Appl. No. 13/770,660, 16 pgs.

* cited by examiner

Smith, John
ACCT #: 0010020030004-1234

[!] ALERTS | DEMOGRAPHICS | COVERAGE | MEDICAL NECESSITY | PRE-CERTIFICATION | ESTIMATE | TRIAGE | COLLECTION

Currently Selected Pool:
Pool Level One (208) ▼

| 74  | Accts Completed in this Pool |
| 118 | Accts Remaining with Alerts |

NEXT ACCOUNT 75 of 208

View Alert Status

OVERVIEW

GENERAL
- 208A [!] QA Alert – Review Patient Registration Form 7 for Accuracy Against Main Data Set on File - 8
- 208B [!] One or More Records Flagged for Review – Line 46
- 208C [!] Check Patient Flow Result for Billing Errors Against BP – Form 26

DEMOGRAPHICS
- 208D [!] Patient DOB in registration does not match patient DOB returned in eligibility. - 6

COVERAGE
- 208E [!] Inactive Coverage
- 208F Medicare A & B
- 208G [!] Medicaid Eligibility Response indicates that patient may have other insurance. Enter PA1 as secondary. -1
- [!] Medicare may be the secondary payer. Review eligibility for additional insurance information. - 7

MEDICAL NECESSITY
- 208H [!] Inpatient Only Procedure Ordered
- 208I [!] ABN Statement Generated
- 208J [!] APC Statement Generated

PRE-CERTIFICATION
- 208K [!] UHC Notice of Admission
- 208L [!] Medicare

CLAIMS
- 208M [!] Missing or Invalid Treatment Authorization
- 208N [!] Missing or Invalid Policy or Group #
- 208O [!] Missing or Invalid Patient DOB Smith, John
0010020030004-1234

[AL] [DG] [CV] [MN] [EST] [TRI] [COL]
Set Account Status ▼  Save

999 Accts I've Cleared Today

Smith, John — 102
ACCT #: 0010020030041234

204 — ALERTS | DEMOGRAPHICS — 212 | COVERAGE — 214 | MEDICAL NECESSITY — 216 | PRE-CERTIFICATION — 218 | ESTIMATE — 220 | TRIAGE — 222 | COLLECTION — 224

Currently Selected Pool: Pool Level One (208)

74 Accts Completed in this Pool
118 Accts Remaining with Alerts

NEXT ACCOUNT — 226
75 of 208

502

202 — DEMOGRAPHICS
204

504 — ☐ Patient
508 — Data Submitted | 510A — USPS® | 510B — Equifax® | 510C — Medicare | 510D — ABC Insurance | 510E — XYZ Insurance

506

| | | | | | |
|---|---|---|---|---|---|
| Name: ☐ | Smith, John | This is a valid address | Smith, Joan | Smith, John | Smith, John | Smith, John |
| SSN: | 538-12-3456 | | 538-12-3456 | 538-12-3456 | 538-12-3456 | 538-12-3456 |
| DOB: | 01/Jan/1921 | | 01/Jan/1921 | 01/Jan/1921 | 01/Jan/1921 | 01/Jan/1921 |
| Address 1: ☐ | 101 Main ST. | | 102 Main ST. | 102 Main ST. | 102 Main ST. | 102 Main S |
| Address 2: | A-1 | | A-1 | A-1 | A-1 | A-1 |
| City: | Middletown | | Middletown | Middletown | Middletown | Middletown |
| State: | TN | | TN | TN | TN | TN |
| Zip: ☐ | 37038 | | 37038 | 37038 | 37738 | 37038 |
| Zip - Ext: | 01256 | | 01256 | 01256 | 01256 | 01256 |

999  Accts I've Cleared Today

[AL] [DG] [CV] [MN] [EST] [TRI] [COL]
Set Account Status ▼   Save

Smith, John
0010020030041234

FIG. 6

Smith, John
ACCT #: 0010020030004-1234

| ALERTS | DEMOGRAPHICS | COVERAGE | MEDICAL NECESSITY | PRE-CERTIFICATION | ESTIMATE | TRIAGE | COLLECTION |

Currently Selected Pool: Pool Level One (208) ▶

74 Accts Completed in this Pool
118 Accts Remaining with Alerts

NEXT ACCOUNT
75 of 208

MEDICAL NECESSITY

☑ Step 1: Pick Procedures

MAMOBI — Mammography Bilateral 77056 ✕
HCFA4538 — Colonoscopy, Flexible - 45383 ✕

☑ Step 2: Pick Diagnosis

GHB — Glycosylated Heoglob - 83036cc Surgery Center ✕

☐ Step 3: Medical Necessity Results

| Alert | Procedures | Status | Document | Amount |
|---|---|---|---|---|
| | Colonoscopy | Signed | | |
| | Appendectomy | ☐ Unsigned | | |
| ABN Statement | | | ABN | $750.00 |
| APC Statement | | | APC | $69.88 |

[AL][DG][CV][MN][EST][TRI][COL]
Set Account Status ▶  Save

Clear all and start over

Launch APC — 710

Smith, John
0010020030004-1234

999 Accts I've Cleared Today

ESTIMATE RESULTS 1008

Estimated Patient Responsibility

$ 895.00

☑ Estimate Printed

Representative Script

The information provided is a hospital estimate and is not a guarantee of final billed charges.

Hospital estimates are based on average charges, and may vary based on the patient's medical condition, unknown circumstances or complications, final diagnosis and recommended treatment ordered by your physician.

Professional fees, such as physician, radiologist, anesthesiologist and pathologist fees are not included in this estimate.

☑ Script Read

1010 Patient

| | |
|---|---|
| Patient Name: | Smith, John |
| Insurance: | Medicare A/B |
| Display Name: | [Medicare A/B] [update] |
| Account Number: | 0010020003004-1234 |
| Policy Number: | ABC-123 |
| Status: | Verified |
| Subscriber Number: | 123123123A |
| Processed On: | Jan/02/2020 |

Discount Plans

| Discount Type | Discount % | Charges | Savings | Amount Due |
|---|---|---|---|---|
| Self-pay ▼ | 10% | $895.00 | $89.50 | $805.50 |
| Prompt-pay ▼ | 15% | $895.00 | $134.25 | $760.75 |

[AL][DG][CV][MN][EST][TR][COL]
Set Account Status ▼  Save          [Update Estimate]  [reset]

Smith, John
0010020003004-1234

999
Accts I've Cleared Today

Smith, John
ACCT #: 0010020003004-1234

| ALERTS | DEMOGRAPHICS | COVERAGE | MEDICAL NECESSITY | PRE-CERTIFICATION | ESTIMATE | TRIAGE | COLLECTION |

Currently Selected Pool: Pool Level One (208)

74 Accts Completed in this Pool
118 Accts Remaining with Alerts

NEXT ACCOUNT 75 of 208

TRIAGE

Financial Assistance
Interview
Note – Household Income

Extended Payment Options:
Collect
From Available Credit

Collections
| Creditor/Type | Original Balance | Current Balance | AMT Paid/Accrued |
| medical/health care | $1,147.00 | $1,010.00 | $137.00 |
| medical/health care | $452.00 | $452.00 | $0 |
| medical/health care | $75.00 | $75.00 | $0 |
| medical/health care | $796.00 | $0 | $796.00 |
| medical/health care | $193.00 | $193.00 | $0 |

Credit Report

```
USER REF.530B8940E-7BCC-48DC-B THIS FORM PRODUCED BY EQUIFAX®
*
SAFESCAN WARNING:
SAFESCANNED: YOUR INQUIRY HAS GONE THROUGH OUR SAFESCAN DATABASE.
*
** ADDRESS DISCREPANCY- NO SUBSTANTIAL DIFFERENCE OCCURRED
------------------------ IDENTIFICATION INFORMATION ------------------------
```

Smith, John
0010020003004-1234

[AL] [DG] [CV] [MN] [EST] [TRI] [COL]
Set Account Status ▸  Save

999 Accts I've Cleared Today

FIG. 11B

Smith, John
ACCT #: 0010020003004-1234

| ALERTS | DEMOGRAPHICS | COVERAGE | MEDICAL NECESSITY | PRE-CERTIFICATION | ESTIMATE | TRIAGE | COLLECTION |

Currently Selected Pool: Pool Level One (208) ▼

74 Accts Completed in this Pool
118 Accts Remaining with Alerts

NEXT ACCOUNT
75 of 208

COLLECTION

Accounts Select a row to "View Account Details"

St Health Hospital
- 10-Oct-2019  112113-114  Past Due  $4,031.29
- 2-Dec-2019   998997-996  Past Due  $935.03
- 15-Dec-2020  556657-656  Payment Due $466.34

Total: $5,432.66

St. Health Physicians
- 112113-114  Payment Due  $45.00

Total: $45.00

[Collect Payment]

Account Detail  ← Back

Charges & Adjustments
- Total Charges ............................... $1,202.89
- Insurance Adjustments ............... -$643.25
- Total Patient Responsibility ......... $559.64
  TOTAL $559.64

Payments to Date
- 1-Nov-2019 .................................. -$31.10
- 2-Dec-2019 .................................. -$31.10
- 2-Jan-2020 ................................... -$31.10
  PAID  $93.30

$ 466.34
Outstanding Balance

Account Status:
Current

Current Terms:
$31.10
for 18 months

[AL][DG][CV][MN][EST][TRI][COL]
Set Account Status ▼  Save

999 Accts I've Cleared Today

Smith, John
0010020003004-1234

FIG. 12A

EXCEPTION-BASED INTEGRATED PATIENT ACCESS WORKFLOW

CROSS-REFERENCE TO RELATED APPLICATIONS

The present application claims priority to U.S. Provisional Patent Application No. 61/600,600 titled "Exception-Based Alert and Prioritization System" filed Feb. 18, 2012, and U.S. Provisional Patent Application No. 61/765,317 titled "Financial Triage" filed Feb. 15, 2013, and is related to U.S. patent application Ser. No. 13/770,660 titled "Account Prioritization for Patient Access Workflow" filed Feb. 19, 2013, the disclosures of which are incorporated herein by reference in their entireties.

BACKGROUND

When a patient seeks healthcare services from a healthcare provider, various processes may be performed between the time when patient data is received and when healthcare services are provided. The various processes may make up a patient access workflow and may include such processes as, but are not limited to, finding coverages (e.g., insurance eligibility and verification), verifying demographic data to help ensure that a patient's demographic data is correct for insurance claims, billing statements, etc., checking payer compliance to help screen for payer medical necessity and precertification and to aid with accuracy in orders, coding and billing, estimating a payment amount, determining a patient's financial situation to help mitigate the risk of late payments and possible need for collections later on, and collecting payment for services.

Currently, the patient access workflow is a fragmented process, wherein various tools may be utilized for different processes. For example, one tool may be utilized for verifying patient demographic information, another tool may be used for checking payer policies, another tool may be used for determining financial eligibility, another tool may be used for determining a best payment method, another tool may be used for payment processing, etc.

As can be appreciated, a fragmented patient access workflow process can be inefficient and can lead to errors. It is with respect to these and other considerations that the present invention has been made.

SUMMARY

Embodiments of the present invention provide an exception-based integrated patient access workflow via a single user interface. When patient data associated with a healthcare encounter is received, various rules may be applied to cross-check the received data with other stored and received data to ensure correct patient data and to ensure accurate information for downstream patient access workflow processes. An indication of discrepant data, missing data, or input/user-interaction that may be needed for performance of a patient access workflow process may be provided. The indication may be provided via alerts displayed in an integrated user interface. Accordingly, a user may be able to address and resolve alerts to ensure patient access workflow processes are performed prior to a healthcare encounter.

BRIEF DESCRIPTION OF DRAWINGS

FIG. 2 is an illustration of an example overview page displaying alerts.

FIG. 3 is an illustration of an example of an alert status UI.

FIG. 5 is an illustration of an example demographics UI page.

FIG. 6 is an illustration of an example coverage UI page.

FIG. 7 is an illustration of an example medical necessity UI page.

FIG. 9 is an illustration of an example estimate UI page.

FIG. 10 is an illustration of an example estimate results UI page.

FIGS. 11A and 11B are illustrations of an example financial clearance UI page.

FIGS. 12A and 12B are illustrations of an example collections UI page.

DETAILED DESCRIPTION

Figure 1:
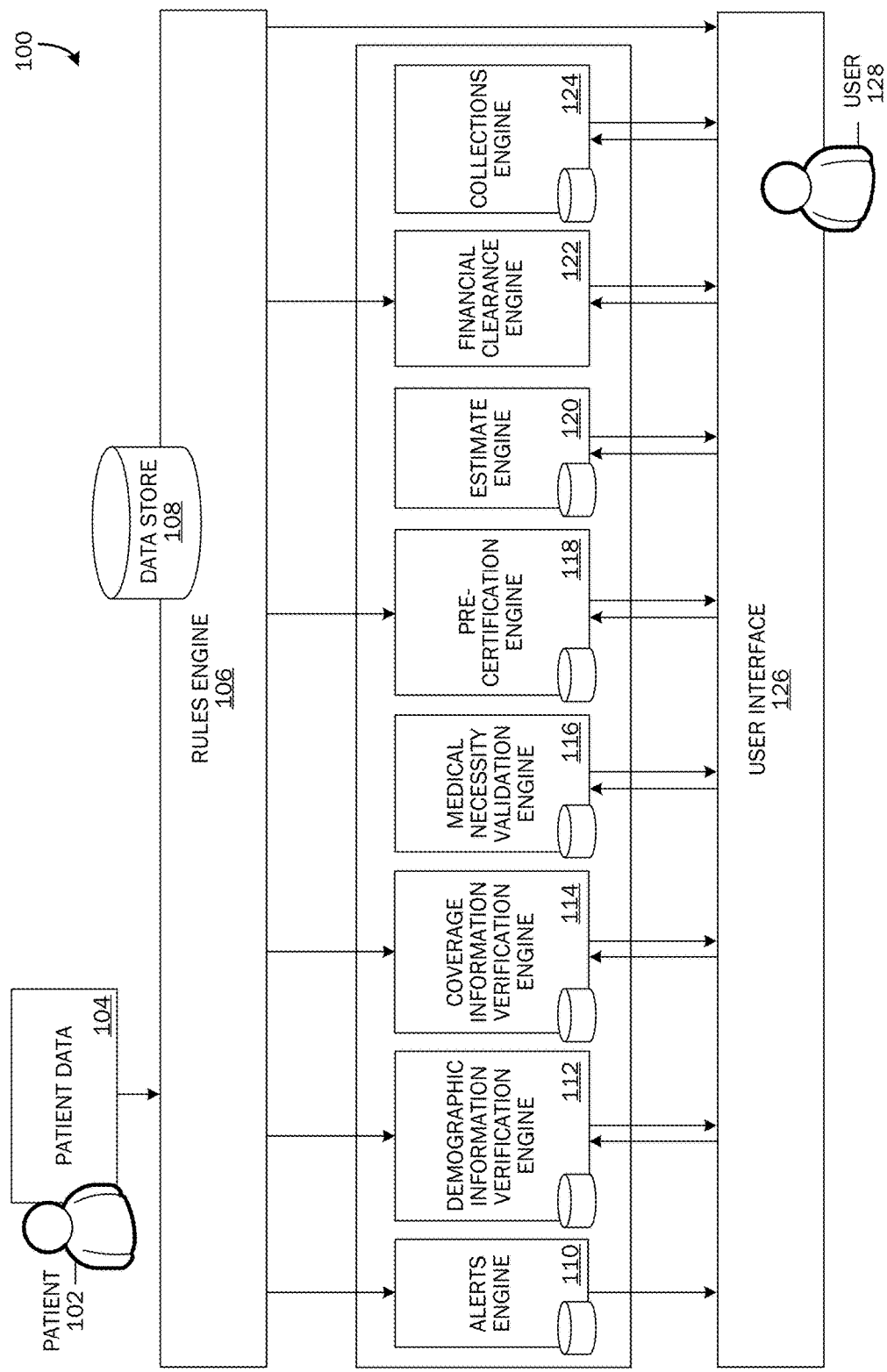
FIG. 1 is a simplified block diagram of a high-level system architecture with which embodiments of the invention may be implemented.

As briefly described above, embodiments of the present invention provide an integrated exception-based patient access workflow. Embodiments may be utilized to help healthcare providers to verify patient information on the front-end, which may lead to a reduction in errors, and clean up on the back-end for ensuring payment certainty. The patient access tool may transform raw information into actionable intelligence and integrate systems and workflows. The patient access tool may modify requests when problems are identified, connect with various payers and various other data sources, and resend requests or sent requests to other payers to get more accurate information.

These embodiments may be combined, other embodiments may be utilized, and structural changes may be made without departing from the spirit or scope of the present invention. The following detailed description is therefore not to be taken in a limiting sense, and the scope of the present invention is defined by the appended claims and their equivalents. Referring now to the drawings, in which like numerals refer to like elements throughout the several figures, embodiments of the present invention and an exemplary operating environment will be described.

Referring now to FIG. 1, a simplified block diagram of a high-level system architecture 100 with which embodiments of the invention may be implemented is shown. Patient data 104 may be inputted into an information system, for example, a healthcare provider information system. Patient data 104 may include one or more of demographics data, admissions data, pre-registration data, coverage data, and scheduling data. If a guarantor of the patient's account is different than the patient 102, patient data 104 may also include data associated with the guarantor. According to embodiments, demographic data may include details of a patient 102 such as, but not limited to, the patient's name, address, phone number(s), social security number, date of birth, gender, marital status, emergency contact information, employment status and details, student status and details, insurance information, guarantor information, etc.

When patient data 104 is received, a rules engine 106 may be triggered to apply various rules and intelligence for verifying the received patient data 104 against data in one or more data sources 108. According to embodiments, according to various rules, requests may be sent automatically to one or more patient access workflow engines 112, 114, 118, 122 to perform one or more patient access workflow processes. According to one embodiment, a rule may be applied to automatically send a request to a demographic information verification engine 112 to cross-match a name, address, etc. of a patient 102 or the guarantor of the patient's account (demographic information included in received patient data 104) with information stored in one or more data sources 108. According to another embodiment, a rule may be applied to automatically send a request to a coverage information verification engine 114 to verify insurance coverages a patient 102 (or guarantor) claims to have. According to another embodiment, a rule may be applied to automatically send a request to a pre-certification engine 118 to identify procedures that may require pre-certification according to a patient's 102 coverage plan. According to another embodiment, a rule may be applied to automatically send a request to a financial clearance engine 122 to collect credit and financial information of a patient 102 (or guarantor of the patient's account) to determine the patient's (or the patient's guarantor's) financial situation. The requests may be sent by the rules engine 106 automatically to one or more patient access workflow engines. That is, a user 128 may not be required to manually send a request to perform a patient access workflow process.

The data sources 108 may store data and metadata such as patient encounter data, patient coverage data, alerts, results from one or more patient access workflow processes, and collections amounts. Stored data and metadata, discrepant or missing patient data 104 may be automatically corrected and/or one or more alerts may be provided. Embodiments may comprise an alerts engine 110 operable to provide alerts to notify a user 128 (e.g., administrative user, patient 102, etc.) of potential problems (e.g., missing information, erroneous information, etc.) or additional steps needed to be completed for performing one or more processes of a patient access workflow. Providing alerts of potential problems or additional steps may provide for an exception-based workflow where a user 128 may be able to address and prioritize accounts with potential problems or accounts needing the attention of a user 128. Accordingly, the user 128 may be able to solve identified problems proactively. According to stored data and metadata, some erroneous or missing information may be automatically corrected.

Results from one or more patient access workflow engines 112, 114, 116, 118, 120, 122, 124 and alerts notifying a user of potential problems or additional actions may be presented via a user interface 126. An example of alerts 208 displayed on a user interface 126 is shown in FIG. 2. The user interface 126 and display of alerts 208 will be described in greater detail below.

With reference again to FIG. 1, the system 100 may comprise a demographic information verification engine 112 operable to verify demographic data to help ensure that a patient's demographic data is correct for insurance claims, billing statements, etc. A request may be sent to a demographic information verification engine 112 either automatically from the rules engine 106 or from a user 128 to cross-match a name, address, etc. of the patient 102 or the guarantor of the patient's account (demographic information included in received patient data 104) with information provided by one or more third party data sources. Incorrect demographic information such as spelling discrepancies, incorrect address information, an incorrect social security number, an incorrect date-of-birth, etc. may be discovered and either automatically corrected or flagged. For more information about one embodiment of a demographic information verification engine 112, please see U.S. patent application Ser. No. 13/651,051 titled "Information Standardization and Verification" filed on Oct. 12, 2012.

The system 100 may also include a coverage information verification engine 114. A request may be sent to the coverage information verification engine 114 either automatically from the rules engine 106 or from a user 128 to perform a coverage (i.e., insurance) eligibility verification process. According to an embodiment, the coverage information verification engine 114 may be operable to perform a query for coverages for a patient 102 (or guarantor). Results from the coverage information verification engine 114 and any alerts may be displayed on the user interface 126.

The system 100 may also include a medical necessity validation engine 116. A request may be sent to the medical necessity validation engine 116 through the user interface 126 to perform a check of a patient order against payer rules for medical necessity, frequency, duplication, modifiers, etc. to help produce a clean claim billed with less chance of denial. For example, medical necessity validation may identify potentially denied claims prior to submission, allowing corrections to take place, eliminating rebilling costs, and increasing staff self-corrections. Based on Medicare and commercial payer rules (e.g., inpatient hospitalization for a treatment that could be safely and adequately provided on an outpatient bases, cosmetic surgery, treatment provided for the convenience of a patient 102, etc.), issues that may result in a denied claim may be detected, and results from the medical necessity validation engine 116 and alerts 208 may be displayed on via the user interface 126.

According to embodiments, the system 100 may also include a pre-certification engine 118. A request may be sent to the pre-certification engine 118 either automatically from the rules engine 106 or from a user 128 through the user interface 126 to identify procedures that may require pre-certification. Results from the pre-certification engine 118 and any alerts 208 of identified procedures requiring a pre-certification may be displayed on the user interface 126.

The system may comprise an estimate engine 120, which may be operable to determine an estimate of an amount a patient 102 (or guarantor) may be expected to pay for healthcare services. A request for an estimate may be sent via the user interface 126. The estimate engine 120 may determine an estimate of a patient's responsibility based on average charges and benefit information such as deductible amounts, co-pay amounts, co-insurance amounts, etc. Results from the estimate engine 120 and alerts 208 may be displayed on the user interface 126.

According to embodiments, a financial clearance engine 122 may be included in the system 100. A request may be sent automatically by the rules engine 106 or by a user 128 via the user interface 126 to the financial clearance engine 122 to communicate with one or more third party data sources to collect credit and financial information of a patient 102 (or guarantor of the patient's account). Collected credit and financial information of a patient 102 (or guarantor of the patient's account) may be utilized to assess a patient's (or guarantor's) financial situation for determining a probability of receiving payment for healthcare services rendered. Results from the financial clearance engine 122 and alerts 208 may be displayed on the user interface 126.

The system 100 may also include a collections engine 124. The collections engine 124 may be operable to help patients know what they owe and how the balance will be paid. For example, the collections engine 124 may provide an explanation to patients about what the patient 102 (or guarantor) will owe at the time of service, may provide an estimate of current services and balances from previous visits, may determine a patient's eligibility for Medicaid and charity before asking for payment, may provide for enrolling eligible patients for Medicaid before rendering service and may extend hospital charity to those who qualify, may securely accept payment upfront for smaller balances, and may extend payment terms and fundraising options for larger balances. Results from the collections engine and alerts 208 may be displayed on the user interface 126.

Having described a high-level system architecture 100 with which embodiments of the invention may be implemented, FIG. 2 illustrates the user interface 126 displaying an overview page 206 of alerts 208 for various patient access workflow processes. As illustrated, the user interface 126 may include a patient's 102 name and account number. Selectable user interface controls 202, 212, 214, 216, 218, 220, 222, 224 may be provided for accessing a user interface page for each of the various patient access workflow processes. For example, selection of an "alerts" user interface (UI) control 202 may provide a display of the overview page 206 as illustrated. Selection of a "demographics" UI control 212 may provide a display of a demographics page as will be described later with reference to FIG. 5. A graphical element, such as an exclamation point icon (herein referred to as an alert icon 204), may be displayed on or near selectable UI controls 202, 212, 214, 216, 218, 220, 222, 224 associated with a patient access workflow process that has an identified issue or alert 208. As illustrated, an alert icon 204 is displayed above the "alerts" UI control 202, the "demographics" UI control 212, a "coverage" UI control 214, a "medical necessity" UI control 216, a "pre-certification" UI control 218, and an "estimate" UI control 220, indicating that one or more alerts 208 have been identified for the demographics, coverage, medical necessity, pre-certification, and estimate processes.

The overview page 206 may provide a display of alerts 208 sorted by category or by patient access workflow process. For example, alerts 208 may be in a general alerts category 210, a demographics alerts category 230, a coverage alerts category 232, a medical necessity alerts category 234, a pre-certification alerts category 236, and a claims alerts category 238.

An alert icon 204 may be displayed with each alert 208. Alert icons 204 may be selectable, wherein selection of an alert icon 204 may provide a display of further information associated with the alert 208 or may provide a display of a UI page of the associated patient access workflow process engine 110, 112, 114, 116, 118, 120, 122, 124. A user 128 may be able to add or edit data, complete a task, etc. to address alerts via UI pages of patient access workflow processes. Patient access workflow process UI pages will be described in further detail with reference to FIGS. 5-12.

A "next" control 226 may be provided, which when selected, may provide a next account for a user 128 to work on next (an account for which to clear alerts 208). A selectable control 228 may also be provided for viewing statuses of alerts 208.

Figure 3:
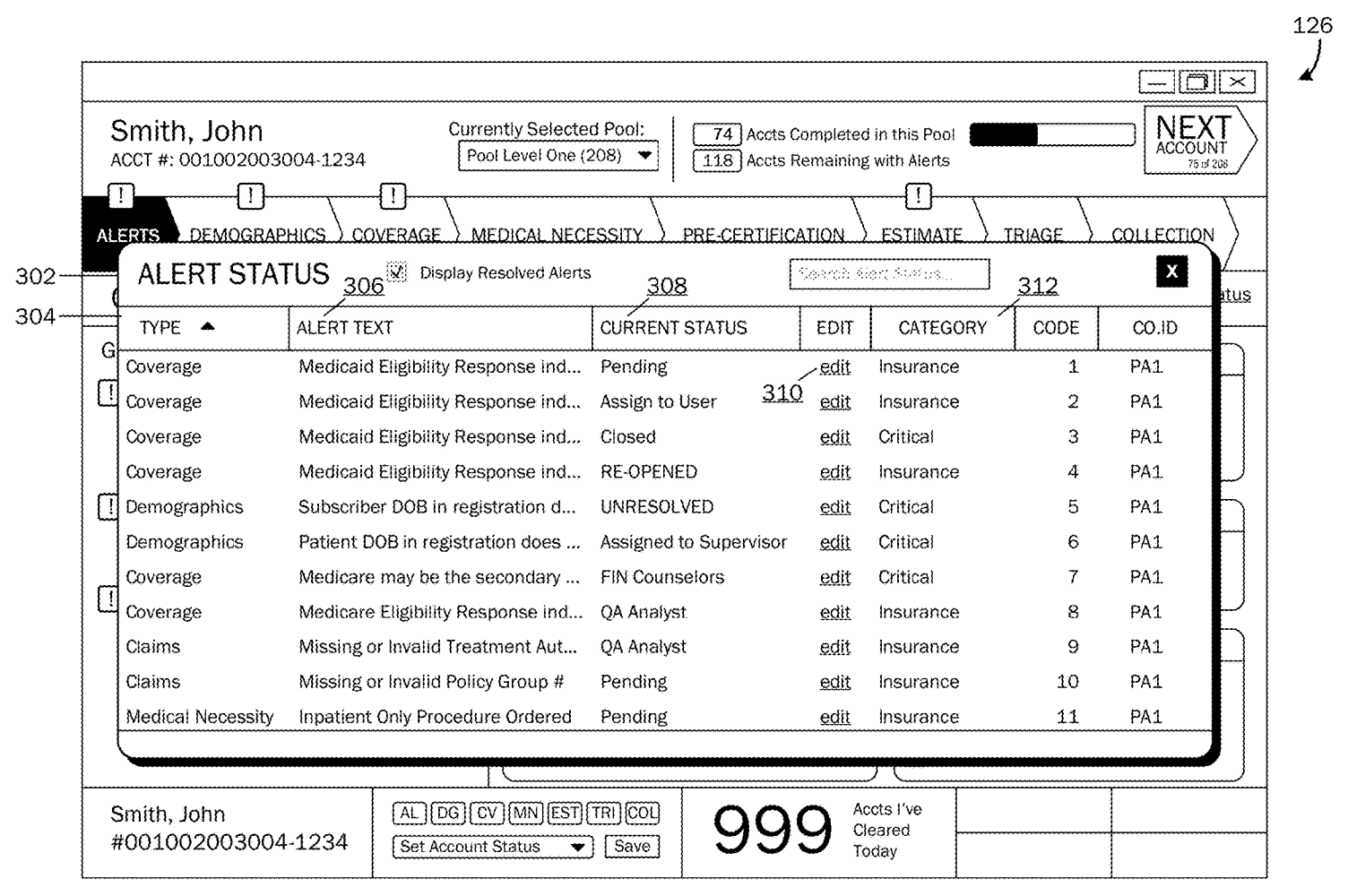

An example of an alert status UI 302 is illustrated in FIG. 3. As illustrated, an alert status UI 302 may include a listing of alerts 208 for a patient's account. The listing may include resolved alerts 208 in addition to unresolved alerts 208, and may include details of each alert 208, such as type 304 (patient access workflow process), alert text (description) 306, current status 308, category 312, etc. An edit functionality 310 may be provided for allowing a user 128 to edit a status of an alert 208.

Figure 4A:
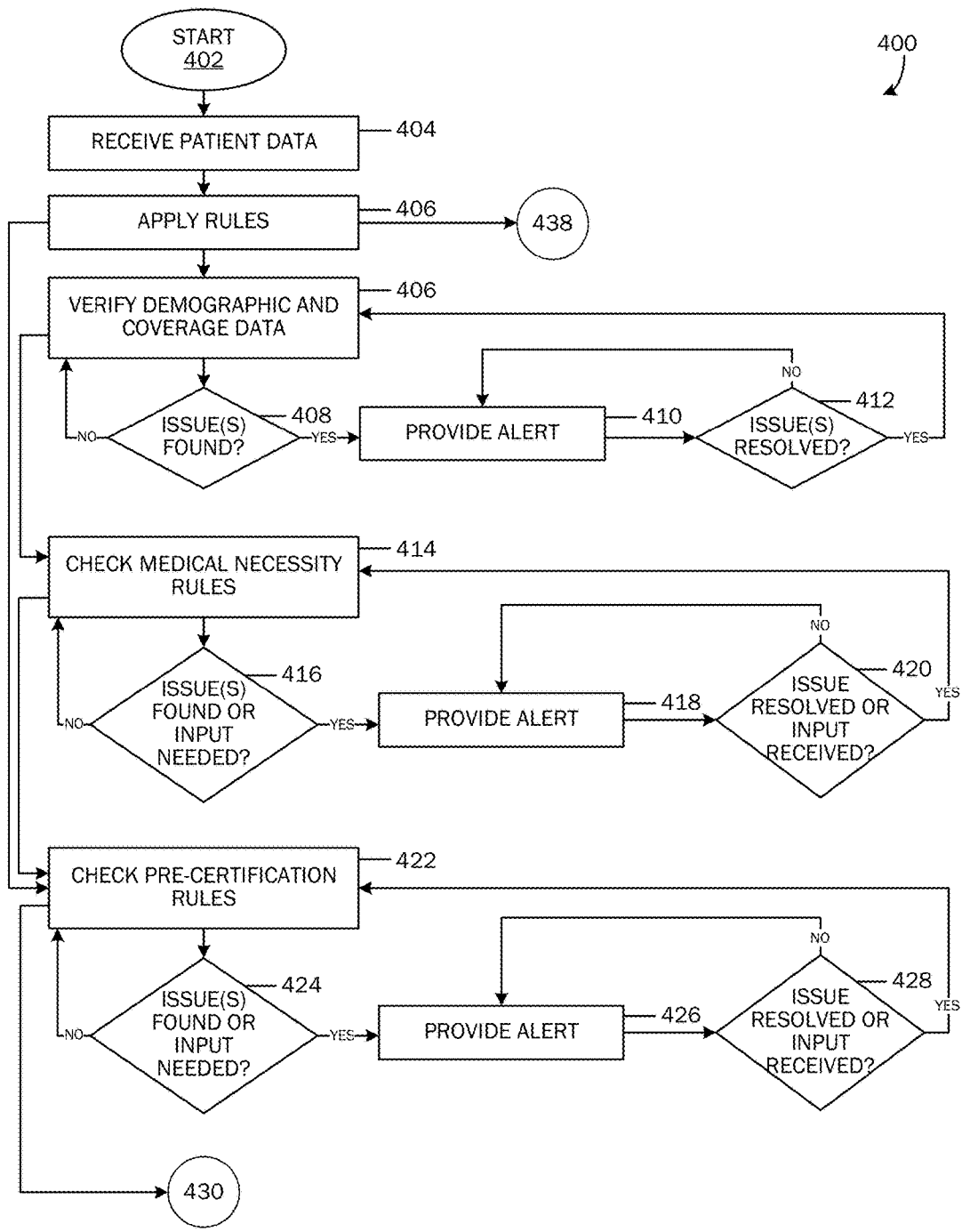
FIGS. 4A and 4B are a flow chart of a method of providing an exception-based integrated patient access in a single user interface according to an embodiment.
Figure 4B:
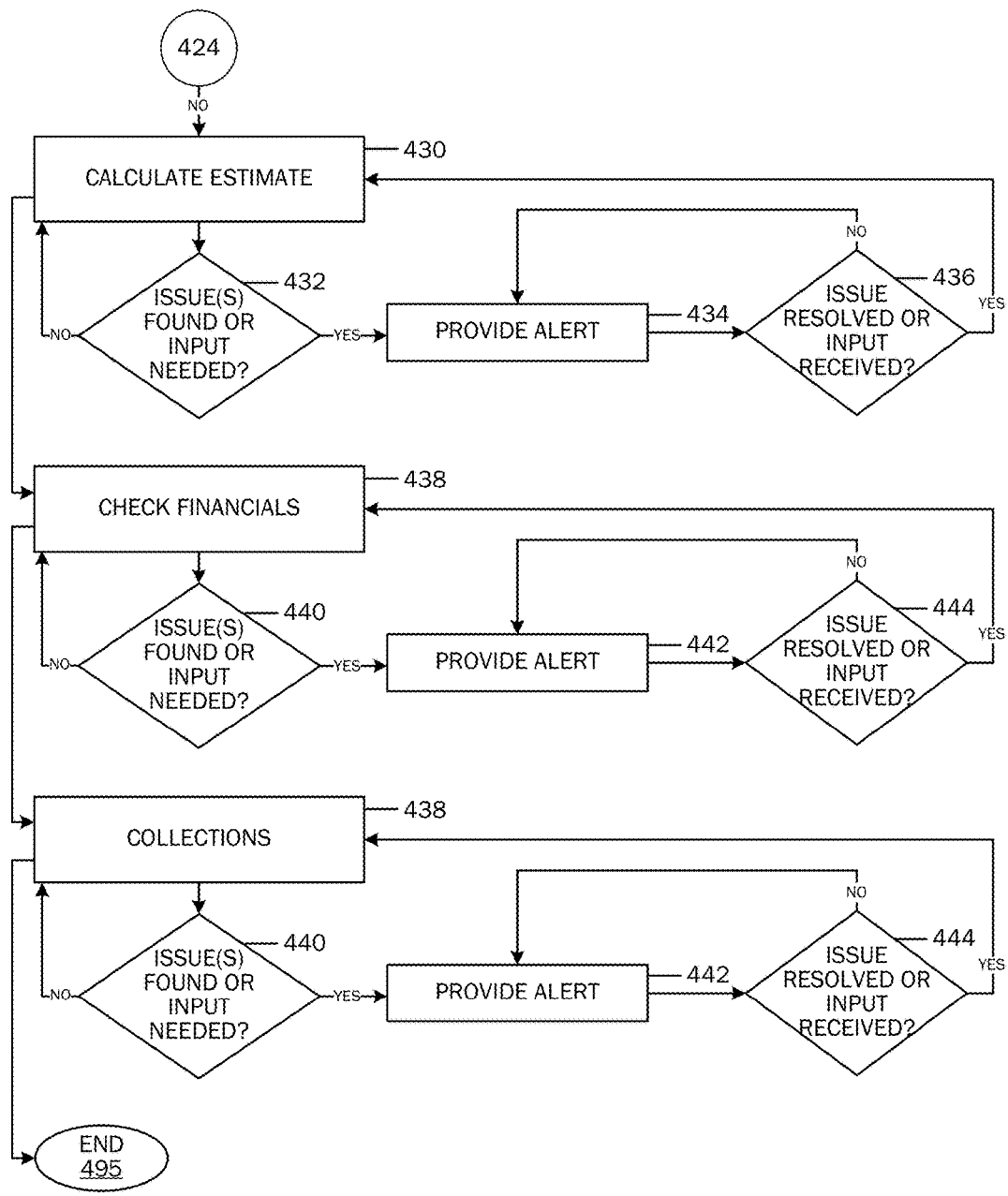

FIGS. 4A and 4B illustrate a flow chart of a method 400 of providing an exception-based integrated patient access in a single user interface according to an embodiment. The method 400 starts at OPERATION 402, and proceeds to OPERATION 404, where patient data 104 may be received. Patient data 104 may be received in association with a healthcare encounter, wherein a healthcare encounter may include, but is not limited to, an appointment, a procedure (e.g., surgical, diagnostic, routine, etc.), an examination, etc. As described above, patient data 104 may include one or more of demographics data, admissions data, pre-registration data, coverage data, and scheduling data and may be entered into an information system, for example, a healthcare provider information system.

When patient data 104 is received, the method 400 may proceed to OPERATION 406, where a rules engine 106 may determine to send a request to a demographic information verification engine 112 to cross-check demographic information in received patient data 104 with data in one or more data sources 108. At OPERATION 406, the rules engine 106 may also determine to send a request to a coverage information verification engine 114 to verify insurance coverage for a patient with one or more payers. According to embodiments, the rules engine 106 may send requests to the pre-certification engine 118 to identify procedures that may require pre-certification according to a patient's 102 coverage plan and/or to the financial clearance engine 122 to determine a patient's 102 financial situation.

At OPERATION 408, a request may be sent to a demographic information verification engine 112 and a coverage information verification engine 114 to verify a patient's 102 (and/or a guarantor of a patient's account) demographic and coverage information provided in received patient data 104. As described above, demographic and coverage information may be cross-checked with data stored in various data stores 108, included third-party databases.

At DECISION OPERATION 410, a determination may be made whether any issues are detected. For example, an issue may be detected if the received patient data 104 differs from stored data, if demographic or coverage data necessary to run one or more of the patient workflow processes is missing, or if user-involvement is needed to perform the demographic or coverage data verification process. If no issues are detected, the demographic information verification engine 112 and the coverage information verification engine 114 may verify the patient's 102 demographic and coverage information at OPERATION 408, or if the demographic and coverage information verification process is complete, the method 400 may proceed to the medical necessity validation process at OPERATION 416.

If issues are detected at DECISION OPERATION 410, the method 400 may proceed to OPERATION 412, where an alert 208 may be provided for each issue detected. According to embodiments, alerts 208 may be provided via the user interface 126 as illustrated in FIG. 5. Referring now to FIG. 5, an example demographics UI page 502 is shown displayed on the user interface 126. The demographics UI page 502 may include results from cross-matching received demographics data (patient data 104) with demographics data provided by one or more third parties 510.

An alert icon 204 may be displayed near patient data 104 that differs from the data provided by one or more third parties 510. For example and as illustrated, an alert icon 204 is displayed next to the patient's name because it does not match the patient's name in one record (from third party 5106) received by the demographic information verification engine 112. As another example, an alert icon 204 is displayed next to the patient's street address because it does not match the patient's street address in any of the displayed records. As another example, an alert icon 204 is displayed next to the patient's ZIP code because a discrepancy is found in the information provided by a third party 510D. As illustrated, data provided by a third party 510 inconsistent with patient data 104 may be marked, for example highlighted, to help a user 128 distinguish conflicting data.

A user 128 may select an alert icon 204 to resolve an issue. According to one embodiment, a user 128 may correct received patient data 104 if it is incorrect. For example and with reference still to FIG. 5, the user 128 may select the alert icon 204 beside the patient's address to correct the patient's street address so that it matches the addresses provided by the third parties 510. The user 128 may take another action, for example, the user may contact the patient 102 to verify his/her address before correcting it. According to embodiments, when information may be edited or added, when a process is performed, a status 308 of an alert 208 has changed, etc., the modified and updated information may be communicated back to the system and stored in the data store 108.

Figure 6:
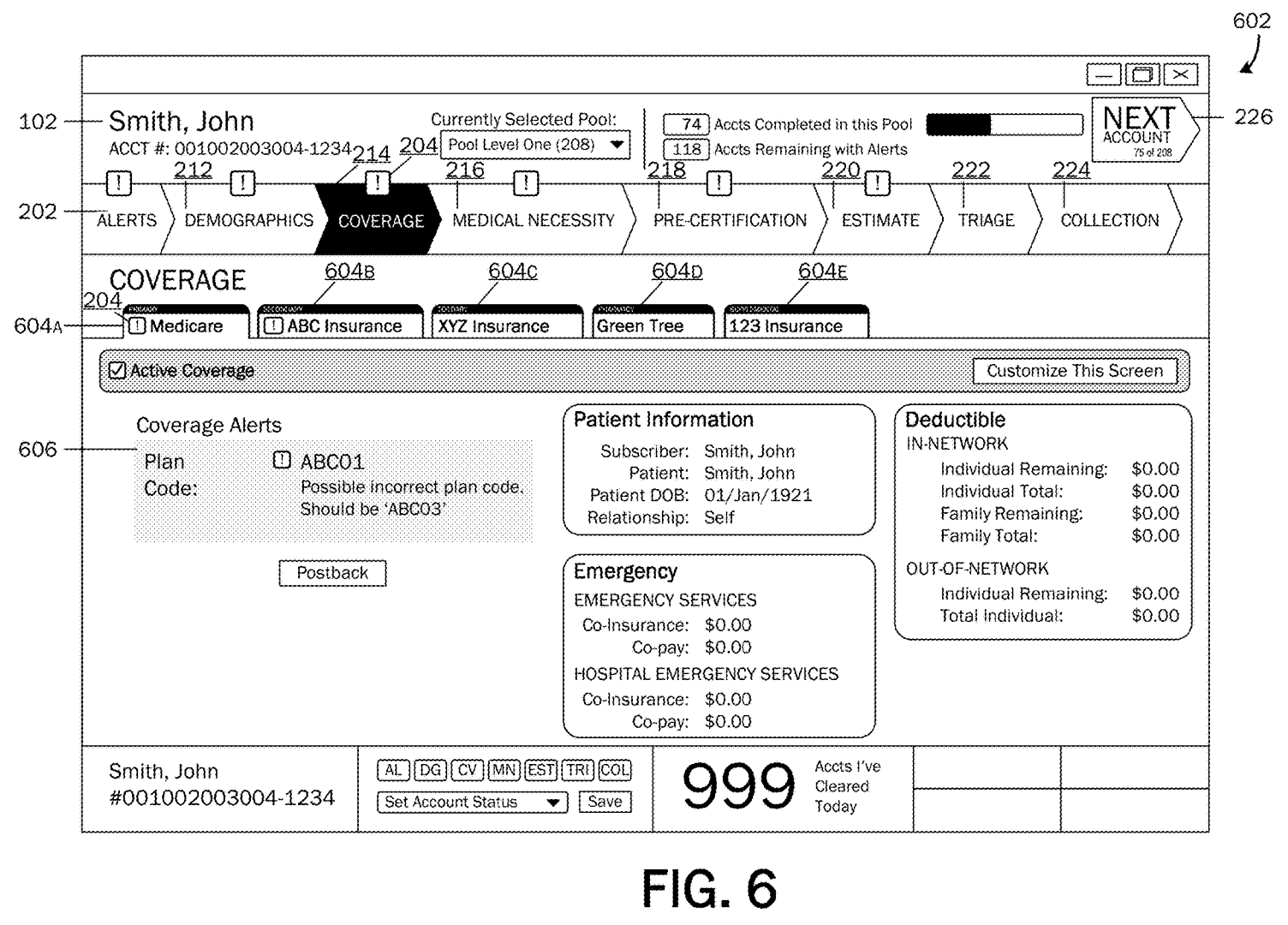

An example coverage UI page 602 displayed on the user interface 126 is illustrated in FIG. 6. The coverage UI page 602 may include results from cross-matching received coverage data (patient data 104) with coverage data provided by one or more coverage providers, herein referred to as payers 604. For example and as illustrated in FIG. 6, an alert icon 204 is displayed where issues have been identified. An alert icon 204 is displayed on two tabs associated with two coverage payers 604A and 604B. An alert 208 is shown displayed in the currently selected tab (associated with payer 604A). For example, a coverage verification alert 208 may be provided if a plan code is identified as an incorrect code. Selection of an alert icon 204 associated with the alert 208 may provide a UI for allowing a user 128 to correct the plan code. The corrected information and changes of status 308 of an alert 208 may be communicated back to the system and stored in the data store 108.

Referring back to FIG. 4A, at DECISION OPERATION 414, a determination may be made whether identified issues have been resolved. That is, a determination may be made whether modified patient data 104 is consistent with stored data or with data provided by one or more third parties 510, if missing data has been provided, and/or if an alert status 308 has been changed to "resolved." If an issue has not been resolved, the method 400 may return to OPERATION 412, where an alert 208 may continue to be associated with the unresolved issue. If the issue(s) have been resolved, the method 400 may return to OPERATION 408, where the demographic and coverage data verification process may be completed, or may proceed to OPERATION 416 to the medical necessity validation process.

At OPERATION 416, a request may be sent to the medical necessity validation engine 116 to detect and provide alerts 208 for issues that may potentially result in a denied claim. At DECISION OPERATION 418, a determination may be made whether any issues are detected or if additional input is needed. For example, an issue may be detected if a selected procedure 704 and/or a selected diagnosis 706 may be determined to not meet medical necessity criteria according to a specified payer's 604 rules. An issue may be detected if user-interaction is needed to perform or complete the medical necessity validation process. If no issues are detected or if no additional input is needed, the medical necessity validation engine 116 may provide medical necessity validation at OPERATION 416, or if the medical necessity validation process is complete, the method 400 may proceed to the pre-certification process at OPERATION 424.

If issues are detected or if additional input is needed at DECISION OPERATION 418, the method 400 may proceed to OPERATION 420, where an alert 208 may be provided for each issue detected. According to embodiments, alerts 208 may be provided via the user interface 126 as illustrated in FIG. 7. Referring now to FIG. 7, an example medical necessity UI page 702 is shown displayed on the user interface 126. As described above, alerts 208 may be provided if additional input or user-interaction is needed. In the medical necessity validation process, an alert 208 may be provided if procedure 704 and/or diagnosis 706 data has not been entered.

Various functionalities may be provided on the medical necessity UI page 702. For example, a procedure 704 selection functionality may be provided, wherein a user 128 may be able to select one or more procedures 704 that may be provided to a patient 102. A diagnosis 706 selection functionality may also be provided, wherein a user 128 may be able to select one or more diagnoses 706 that has been given to a patient 102. The medical necessity UI page 702 may include results 708 from the medical necessity validation engine 116. According to an embodiment, an alert may be provided for an additional step needing to be performed. For example and as illustrated, an alert icon 204 is shown displayed in the medical necessity results 708, indicating that an APC statement (Ambulatory Payment Classification statement) may need to be completed for a specified procedure 704. A selectable functionality control 710 may be provided for launching an APC statement generator. According to embodiments, when information may be edited or added, when a process is performed, a status 308 of an alert 208 has changed, etc., the modified and updated information may be communicated back to the system and stored in the data store 108.

Referring back to FIG. 4A, at DECISION OPERATION 422, a determination may be made whether identified issues have been resolved. That is, a determination may be made whether additional input is needed, if all medical necessity validation process steps have been performed, and/or if an alert status 308 has been changed to "resolved." If an issue has not been resolved, the method 400 may return to OPERATION 420, where an alert 208 may continue to be associated with the unresolved issue. If the issue(s) have been resolved, the method 400 may return to OPERATION 416, where the medical necessity validation process may be completed, or may proceed to OPERATION 424 to the pre-certification process.

At OPERATION 424, a request may be sent to the pre-certification engine 118 to determine if pre-certification is required and to request authorization for procedures determined to require pre-certification. At DECISION OPERATION 426, a determination may be made whether any issues are detected or if additional input is needed. For example, an issue may be detected if a selected procedure 704 may be determined to require pre-certification according to a specified payer's 604 rules. An issue may be detected if user-interaction is needed to perform or complete the pre-certification process. If no issues are detected or if no additional input is needed, the pre-certification engine 118 may perform pre-certification at OPERATION 424, or if the pre-certification process is complete, the method 400 may proceed to the estimate process at OPERATION 432.

Figure 8:
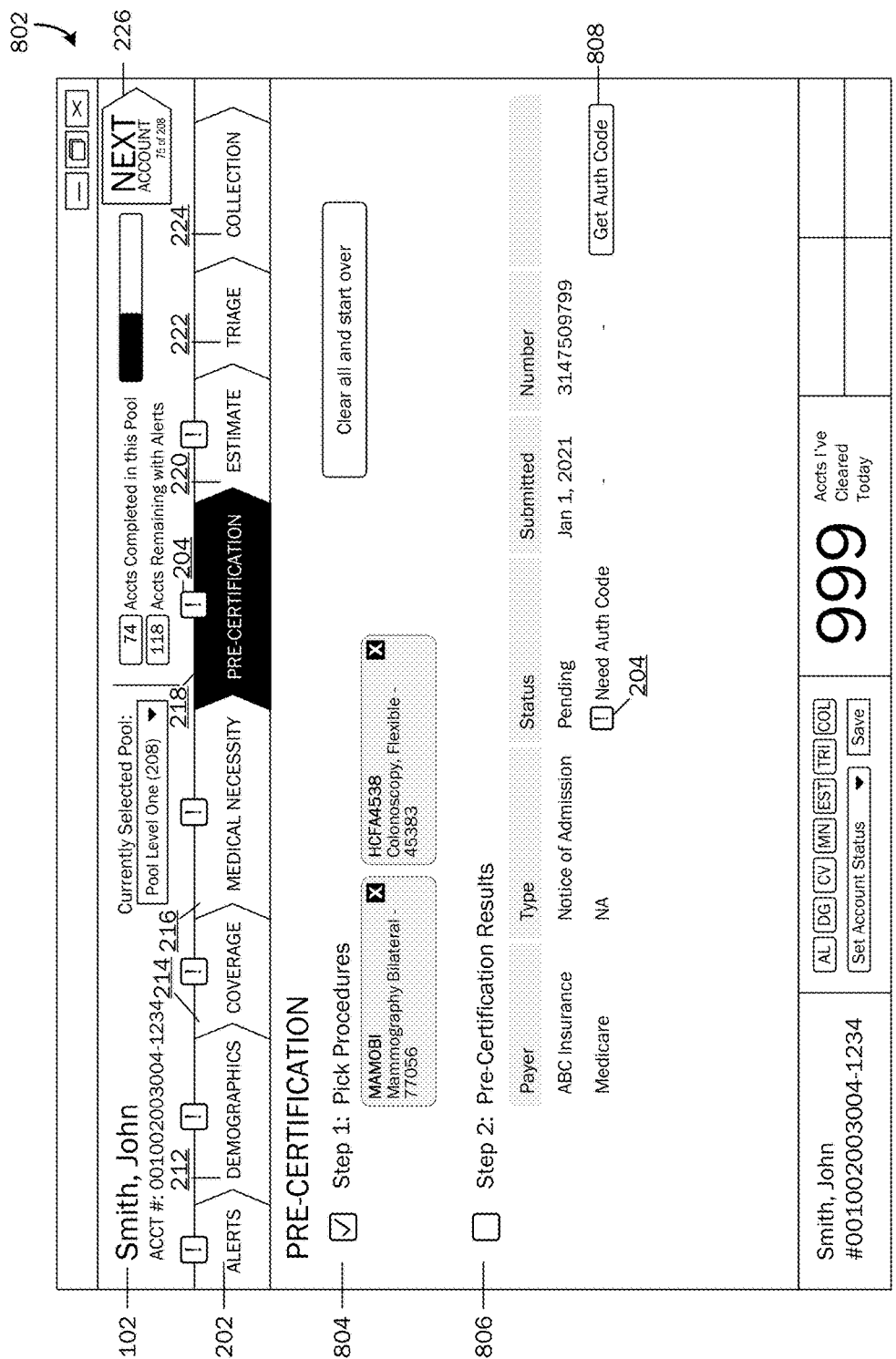
FIG. 8 is an illustration of an example pre-certification UI page.

If issues are detected or if additional input is needed at DECISION OPERATION 426, the method 400 may proceed to OPERATION 428, where an alert 208 may be provided for each issue detected. According to embodiments, alerts 208 may be provided via the user interface 126 as illustrated in FIG. 8. Referring now to FIG. 8, an example pre-certification UI page 802 is shown displayed on the user interface 126. As described above, alerts 208 may be provided if additional input or user-interaction is needed. In the pre-certification process, an alert 208 may be provided if procedure 704 data has not been entered.

Various functionalities may be provided on the pre-certification UI page 802. For example, a procedure 704 selection functionality may be provided, wherein a user 128 may be able to select one or more procedures 704 that may be provided to a patient 102. The pre-certification UI page 802 may include results 806 from the pre-certification engine 118. According to an embodiment, an alert may be provided for an additional step needing to be performed. For example and as illustrated, an alert icon 204 is shown displayed in the pre-certification results 806, indicating that an authorization code may be needed from a specified payer 604 for a specified procedure 704. A selectable functionality control 808 may be provided for requesting an authorization code from a payer 604. Edited or added information, data from performed processes, alert status 308 changes, etc., may be communicated back to the system and stored in the data store 108.

Referring back to FIG. 4A, at DECISION OPERATION 430, a determination may be made whether identified issues have been resolved. That is, a determination may be made whether additional input is needed, if all pre-certification process steps have been performed, and/or if an alert status 308 has been changed to "resolved." If an issue has not been resolved, the method 400 may return to OPERATION 428, where an alert 208 may continue to be associated with the unresolved issue. If the issue(s) have been resolved, the method 400 may return to OPERATION 424, where the pre-certification process may be completed, or may proceed to OPERATION 432 to the estimate process.

The method 400 continues on FIG. 4B. At OPERATION 432, a request may be sent to the estimate engine 120 to determine an estimate of an amount a patient 102 (or guarantor) may be expected to pay for healthcare services. At DECISION OPERATION 434, a determination may be made whether any issues are detected or if additional input is needed. For example, an issue may be detected if a user 128 has not yet selected a procedure 704 for calculating an estimate. An issue may be detected if user-interaction is needed to perform or complete the estimate calculation process. If no issues are detected or if no additional input is needed, the estimate engine 120 may calculate an estimate at OPERATION 432, or if the estimate process is complete, the method 400 may proceed to the financial clearance process at OPERATION 440.

Figure 9:
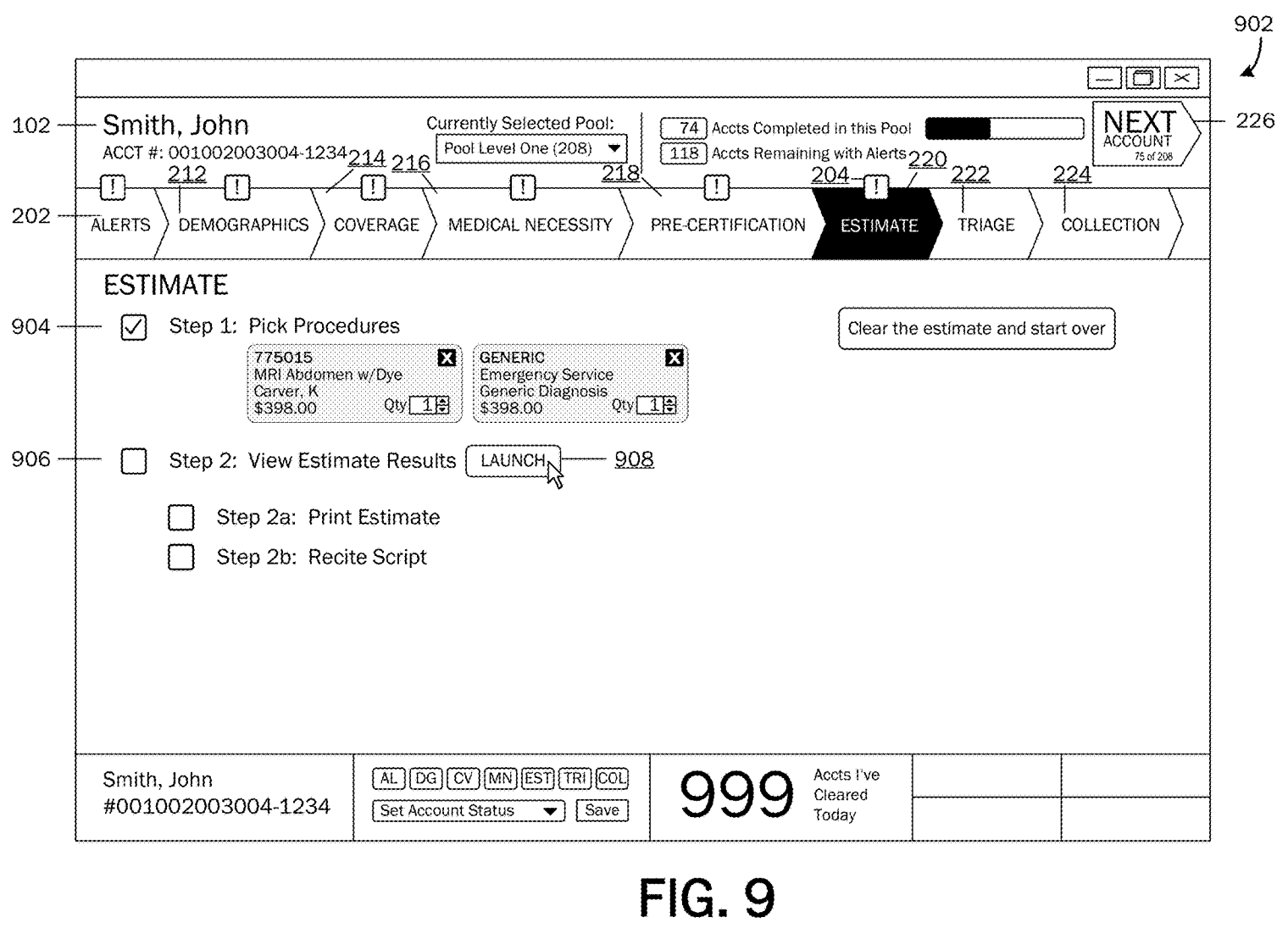

If issues are detected or if additional input is needed at DECISION OPERATION 434, the method 400 may proceed to OPERATION 436, where an alert 208 may be provided for each issue detected. According to embodiments, alerts 208 may be provided via the user interface 126 as illustrated in FIG. 9. Referring now to FIG. 9, an example estimate UI page 902 is shown displayed on the user interface 126. As described above, alerts 208 may be provided if additional input or user-interaction is needed. In the estimate process, an alert 208 may be provided if procedure 704 data has not been entered for calculating an estimate.

Various functionalities may be provided on the estimate UI page 902. For example, a procedure 704 selection functionality may be provided, wherein a user 128 may be able to select one or more procedures 704 that may be provided to a patient 102. The pre-certification UI page 902 may include results from the estimate engine 120. According to an embodiment, an alert may be provided for an additional step needing to be performed. For example, an alert icon 204 may be displayed indicating that a procedure 704 may need to be selected to calculate an estimate. A selectable functionality control 908 may be provided for launching the estimate engine 120. Edited or added information, data from performed processes, alert status 308 changes, etc., may be communicated back to the system and stored in the data store 108.

An example of an estimate results UI 1004 is illustrated in FIG. 10. The estimate results UI 1004 may include an estimate 1006 of a patient's responsibility. A script 1008 may also be provided for informing the patient 102 that the estimate 1006 is not a guarantee of final billed charges. The estimate results UI 1004 may include patient information 1010 and may include functionalities 1012 for applying discounts to an estimate 1006. Calculated and modified data may be communicated back to the system and stored in the data store 108.

Referring back to FIG. 4B, at DECISION OPERATION 438, a determination may be made whether identified issues have been resolved. That is, a determination may be made whether additional input is needed, if all estimate process steps have been performed, and/or if an alert status 308 has been changed to "resolved." If an issue has not been resolved, the method 400 may return to OPERATION 436, where an alert 208 may continue to be associated with the unresolved issue. If the issue(s) have been resolved, the method 400 may return to OPERATION 432, where the estimate calculation process may be completed, or may proceed to OPERATION 440 to the financial clearance process.

At OPERATION 440, a request may be sent to the financial clearance engine 122 to determine a patient's 102 (or guarantor's) ability to pay, to determine if a patient 102 may need to pay upfront for services (for example, if a determination is made that the patient has a history of unpaid medical bills), if the patient qualifies for charity care or financial assistance. At DECISION OPERATION 442, a determination may be made whether any issues are detected or if additional input is needed. For example, an issue may be detected if a patient 102 has a low credit score, owes for past medical bills, has a history of not paying for medical bills, qualifies for financial assistance, etc.). If no issues are detected or if no additional input is needed, the financial clearance engine 122 may request finance information from one or more data sources, including one or more third parties, and determine a financial assessment of a patient 102 (or guarantor) at OPERATION 440, or if the financial clearance process is complete, the method 400 may proceed to the collections/payment processing process at OPERATION 448.

Figure 11A:
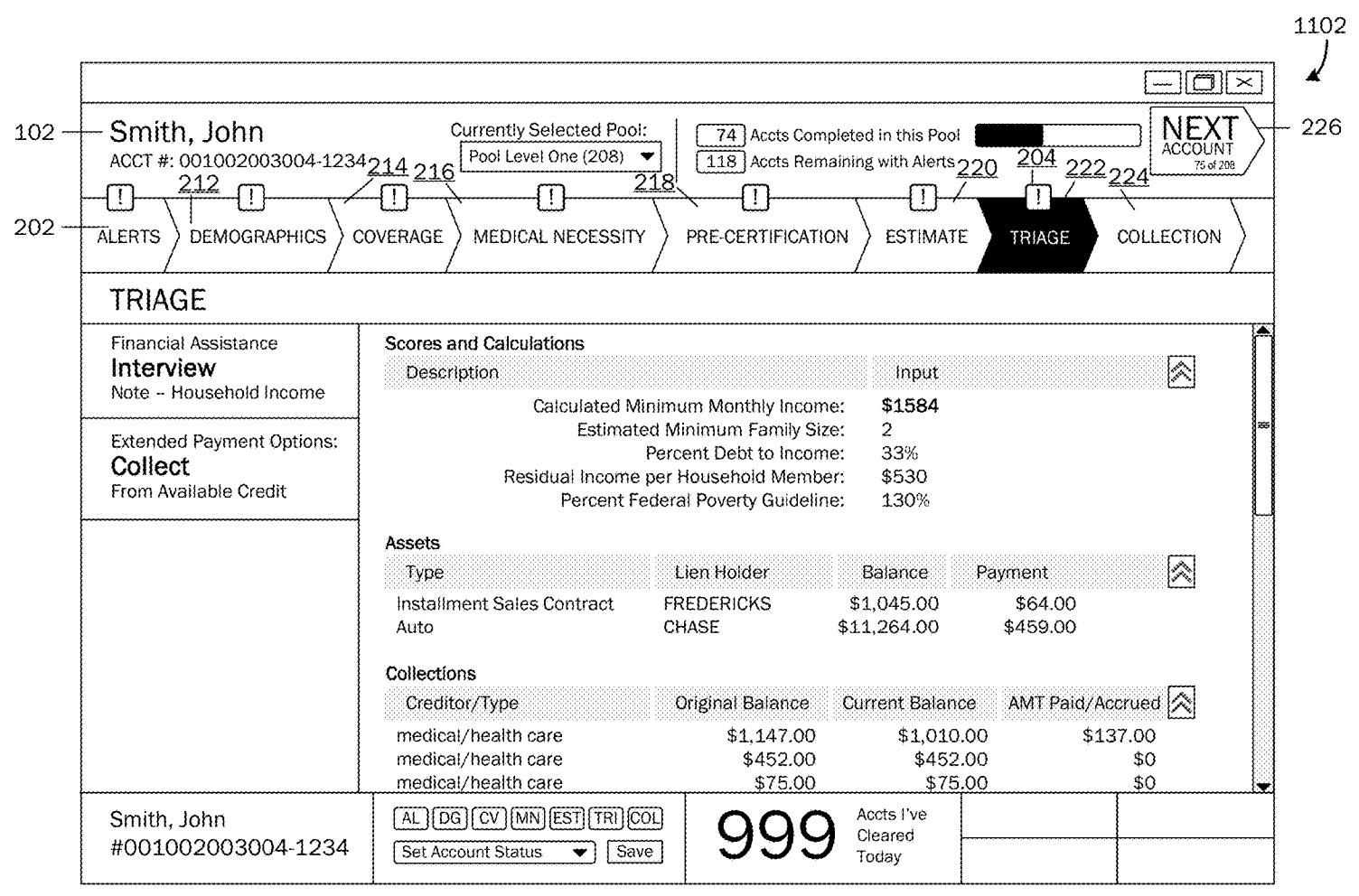

If issues are detected or if additional input is needed at DECISION OPERATION 442, the method 400 may proceed to OPERATION 444, where an alert 208 may be provided for each issue detected. According to embodiments, alerts 208 may be provided via the user interface 126 as illustrated in FIGS. 11A and 11B. Referring now to FIGS. 11A and 11B, an example financial clearance ("triage") UI page 702 is shown displayed on the user interface 126. As described above, alerts 208 may be provided if an issue is detected that may indicate a risk of receiving payment for healthcare services provided to a patient 102.

The financial clearance UI page 1102 may include results 1106 from the financial clearance engine 122. For example and as illustrated, a listing of a patient's assets, credit scores, collections, debt-to-income ratio, income, credit report, etc. may be displayed. According to an embodiment, alerts 208 may include recommended steps to mitigate the risk of non-payment. For example and as illustrated, an alert 208 may include a recommended step to interview a patient for financial assistance. Edited or added information, data from performed processes, alert status 308 changes, etc., may be communicated back to the system and stored in the data store 108.

Referring back to FIG. 4B, at DECISION OPERATION 446, a determination may be made whether identified issues have been resolved. That is, a determination may be made whether additional input is needed, if all financial clearance process steps have been performed, and/or if an alert status 308 has been changed to "resolved." If an issue has not been resolved, the method 400 may return to OPERATION 444, where an alert 208 may continue to be associated with the unresolved issue. If the issue(s) have been resolved, the method 400 may return to OPERATION 440, where the financial clearance process may be completed, or may proceed to OPERATION 448 to the collections/payment processing process.

At OPERATION 448, a request may be sent to the collections engine 124 to provide an amount owed for current services rendered, past services rendered, as well as an estimate of future services, register a patient 102 for financial assistance or charity to those who qualify, may securely accept payment upfront, and may extend payment terms and fundraising options for balances.

At DECISION OPERATION 450, a determination may be made whether any issues are detected or if additional input is needed. For example, an issue may be detected if a patient 102 has a past due amount, if an upfront payment is suggested, if the patient 102 qualifies for financial assistance, etc. Additionally, a payment plan may be set up. If no issues are detected or if no additional input is needed, at OPERATION 448, the collections engine 124 may provide a listing of past, current balances, and estimated costs for scheduled services. Payment for services may also be collected at OPERATION 448. If the collections process is complete, the method 400 may end at OPERATION 498.

Figure 12B:
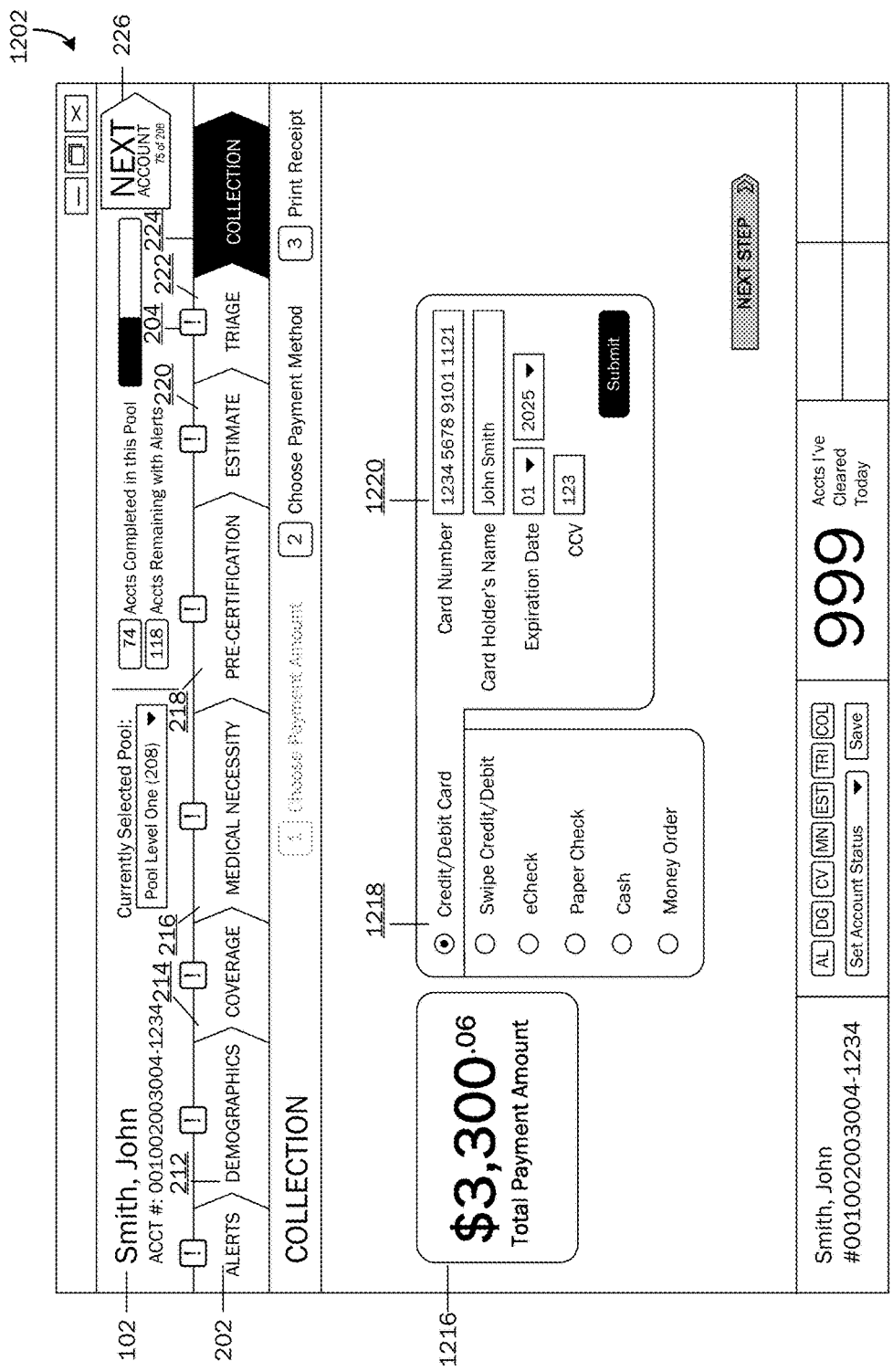

If issues are detected or if additional input is needed at DECISION OPERATION 450, the method 400 may proceed to OPERATION 452, where an alert 208 may be provided for each issue detected. According to embodiments, alerts 208 may be provided via the user interface 126. FIG. 12A shows an example of a collections UI page 1202 displayed on the user interface 126. The collections UI page 1202 may include a listing of a patient's accounts 1204, including amounts owed on the accounts 1204. A selectable control 1206 may be provided with owed amounts, which when selected, may provide billing details 1208 of the account. A current outstanding balance 1210, a current account status 1212, and if applicable, financing terms 1214 may be displayed. As described above, payment on an account may be collected via the collections UI page 1202 as illustrated in FIG. 12B. Functionalities may be provided for selecting a payment amount 1216, for selecting a payment method 1218, and for entering payment information 1220. When a payment is made on an account, the updated billing information may be communicated back to the system and stored in the data store 108.

Referring back to FIG. 4B, at DECISION OPERATION 454, a determination may be made whether identified issues have been resolved. That is, a determination may be made whether additional input is needed, if payment information is correct and/or authorized, if all collections process steps have been performed, and/or if an alert status 308 has been changed to "resolved." If an issue has not been resolved, the method 400 may return to OPERATION 452, where an alert 208 may continue to be associated with the unresolved issue. If the issue(s) have been resolved, the method 400 may return to OPERATION 448, where the collections process may be completed, or may end at OPERATION 498.

Embodiments of the invention may be implemented via local and remote computing and data storage systems. Such memory storage and processing units may be implemented in a computing device, such as computing device 1300 of FIG. 13. Any suitable combination of hardware, software, or firmware may be used to implement the memory storage and processing unit. For example, the memory storage and processing unit may be implemented with computing device 1300 or any other computing devices 1318, in combination with computing device 1300, wherein functionality may be brought together over a network in a distributed computing environment, for example, an intranet or the Internet, to perform the functions as described herein. Such systems, devices, and processors (as described herein) are examples and other systems, devices, and processors may comprise the aforementioned memory storage and processing unit, consistent with embodiments of the invention.

Figure 13:
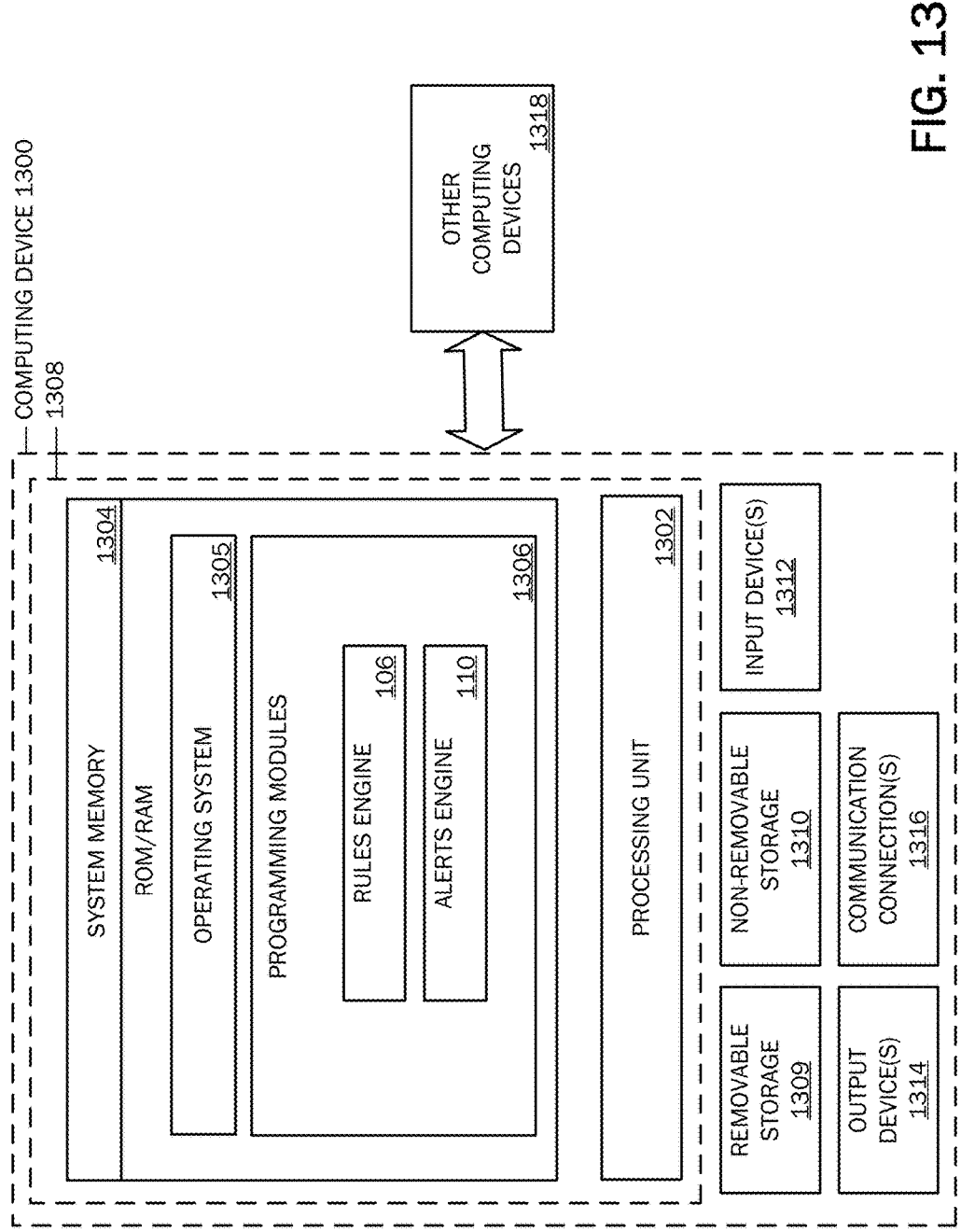
FIG. 13 is a simplified block diagram of a computing device with which embodiments of the present invention may be practiced.

With reference to FIG. 13, a system consistent with embodiments of the invention may include one or more computing devices, such as computing device 1300. The computing device 1300 may include at least one processing unit 1302 and a system memory 1304. The system memory 1304 may comprise, but is not limited to, volatile (e.g. random access memory (RAM)), non-volatile (e.g. read-only memory (ROM)), flash memory, or any combination. System memory 1304 may include operating system 1305, one or more programming modules 1306, and may include a rules engine 106 and an alerts engine 110, wherein the rules engine 106 and the alerts engine 110 are software applications having sufficient computer-executable instructions, which when executed, performs functionalities as described herein. Operating system 1305, for example, may be suitable for controlling computing device 1300's operation. Furthermore, embodiments of the invention may be practiced in conjunction with a graphics library, other operating systems, or any other application program and is not limited to any particular application or system. This basic configuration is illustrated in FIG. 13 by those components within a dashed line 1308. Computing device 1300 may also include one or more input device(s) 1312 (keyboard, mouse, pen, touch input device, etc.) and one or more output device(s) 1314 (e.g., display, speakers, a printer, etc.).

Although embodiments of the present invention have been described as being associated with data stored in memory and other storage mediums, data can also be stored on or read from other types of computer-readable media, such as secondary storage devices, like hard disks, floppy disks, or a CD-ROM, a carrier wave from the Internet, or other forms of RAM or ROM. Further, the disclosed methods' stages may be modified in any manner, including by reordering stages and/or inserting or deleting stages, without departing from the invention.

The computing device 1300 may also include additional data storage devices (removable and/or non-removable) such as, for example, magnetic disks, optical disks, or tape. Such additional storage is illustrated in FIG. 13 by a removable storage 1309 and a non-removable storage 1310. Computing device 1300 may also contain a communication connection 1316 that may allow device 1300 to communicate with other computing devices 1318, such as over a network in a distributed computing environment, for example, an intranet or the Internet. Communication connection 1316 is one example of communication media.

Program modules, such as the rules engine 106 and the alerts engine 110, may include routines, programs, components, data structures, and other types of structures that may perform particular tasks or that may implement particular abstract data types. Moreover, embodiments of the invention may be practiced with other computer system configurations, including hand-held devices, multiprocessor systems, microprocessor-based or programmable user electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general purpose computer or in any other circuits or systems.

Embodiments of the invention, for example, may be implemented as a computer process (method), a computing system, or as an article of manufacture, such as a computer program product or computer readable media. The computer program product may be a computer storage media readable by a computer system and encoding a computer program of instructions for executing a computer process. Accordingly, the present invention may be embodied in hardware and/or in software (including firmware, resident software, microcode, etc.). In other words, embodiments of the present invention may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

Embodiments of the present invention, for example, are described above with reference to block diagrams and/or operational illustrations of methods, systems, and computer program products according to embodiments of the invention. For example, FIGS. 1-13 and the described functions taking place with respect to each illustration may be considered steps in a process routine performed by one or more local or distributed computing systems. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While the specification includes examples, the invention's scope is indicated by the following claims. Furthermore, while the specification has been described in language specific to structural features and/or methodological acts, the claims are not limited to the features or acts described above. Rather, the specific features and acts described above are disclosed as example for embodiments of the invention.

It will be apparent to those skilled in the art that various modifications or variations may be made in the present invention without departing from the scope or spirit of the invention. Other embodiments of the invention will be apparent to those skilled in the art from consideration of the specification and practice of the invention disclosed herein.

All rights including copyrights in the code included herein are vested in and the property of the Applicant. The Applicant retains and reserves all rights in the code included herein, and grants permission to reproduce the material only in connection with reproduction of the granted patent and for no other purpose.

We claim:

1. A system to transform raw information into actionable intelligence and integrate workflows via an integrated user interface (UI) comprising:
   a computer processor; and
   a computer storage device that stores instructions that, when executed by the computer processor, integrates outputs of a plurality of workflow engines to generate the integrated UI to display and enable resolution of generated alerts via the integrated UI according to the outputs of the plurality of workflow engines, the instructions to:
   enable a display of a first selectable control with the integrated UI that, when selected, operates to display a demographics UI display as part of the integrated UI;
   in response to selection of the first selectable control of the integrated UI, display the demographics UI display with data provided by a first workflow engine comprising a demographic information verification engine, wherein the demographics UI display displays alerts with patient data that differs from the demographic data stored in one or more third party data sources and marks conflicting demographic data provided by the one or more third party data sources;
   enable a display of a second selectable control with the integrated UI that, when selected, operates to display a coverage UI display as part of the integrated UI;
   in response to selection of the second selectable control of the integrated UI, display the coverage UI display with data provided by a second workflow engine comprising a coverage information verification engine, wherein the coverage UI display displays coverage verification alerts for coverage issues identified between the patient data and coverage information received from the one or more third party data sources;
   enable a display of a third selectable control with the integrated UI that, when selected, operates to display an alert overview UI display as part of the integrated UI; and
   in response to selection of the third selectable control of the integrated UI, display the alert overview UI display with alert data provided by a third workflow engine comprising an alerts engine, the alert overview UI display including an alert status UI display that displays resolved and/or unresolved alerts with alert details that include a type of alert, a current alert status, and an alert category, wherein the demographic information verification engine outputs the data for the demographics UI display of the integrated UI after cross-matching the patient data with the demographic data stored in the one or more third party data sources to determine if any demographic data is missing from the patient data and that the demographic data in the patient data is consistent with the demographic data stored in the one or more third party data sources, the coverage information verification engine outputs the data for the coverage UI display of the integrated UI after performing a query for coverages claimed by a patient or guarantor corresponding with the patient data and after cross-matching the patient data with insurance coverage data stored in the one or more third party data sources to determine if the coverage data is missing from the patient data and that the coverage data in the patient data is consistent with the coverage data stored in the one or more third party data sources, and the alerts engine outputs the alert data for the alert overview UI display and one or more of the demographics UI display and the coverage UI display and generates one or more displayable alerts for display in the alert overview UI display and in one or more of the demographics UI display and the coverage UI display corresponding to the alert data affecting one or more downstream patient access workflow processes that depend on accurate data.

2. The system of claim 1, further comprising a pre-certification engine to identify procedures that require pre-certification according to the coverage data, wherein the alerts engine generates general alerts, demographics alerts, coverage alerts, medical necessity alerts, pre-certification alerts, and claims alerts.

3. The system of claim 2, further to generate displayable alerts based on outputs from:
the demographic information verification engine;
the coverage information verification engine;
a medical necessity validation engine;
a pre-certification engine;
an estimate engine;
a financial clearance engine; and
a collections engine.

4. The system of claim 2, further comprising:
a data store, wherein the system receives input in response to a displayed alert via the integrated UI, updates an alert status for the displayed alert in response to the received input, and stores the received input and the updated alert status in the data store.

5. The system of claim 1, further to generate alerts associated with:
medical necessity validation;
pre-certification;
estimation;
financial clearance; or
collections.

6. The system of claim 5, further to generate an alert associated with a patient access workflow process requiring a resolving input.

7. The system of claim 6, further to display a selectable alert icon for each alert, wherein selection of the alert icon provides a display of a description of the resolving input that resolves the alert associated with a corresponding patient access workflow process, wherein the system updates and stores a status of the alert after the resolving input.

8. The system of claim 6, further to determine if a patient access workflow process requires a resolving input comprising a selected procedure or a diagnosis.

9. The system of claim 1, further to display a selectable alert icon for each alert, wherein selection of the selectable alert icon displays a description of the missing or inconsistent demographic or coverage data.

10. The system of claim 1, further to resolve alerts associated with:
the demographic information verification engine;
the coverage information verification engine;
a medical necessity validation engine;
a pre-certification engine;
an estimate engine;
a financial clearance engine; and
a collections engine.

11. The system of claim 1, to access one or more downstream patient access workflow processes that comprise one or more of:
medical necessity validation;
pre-certification;
estimation;
financial clearance; or
collections.

12. The system of claim 11, further operable to:
determine if user input is required for performing one or more of the one or more downstream patient access workflow processes; and
if user input is required for performing a downstream patient access workflow process, provide an alert associated with the patient access workflow process requiring user input.

13. The system of claim 12, to display a selectable alert icon associated with a patient access workflow process, wherein selection of the selectable alert icon provides a display of a description of resolving input.

14. A non-transitory computer readable medium containing computer executable instructions which, when executed, transform raw information into actionable intelligence and integrate workflows via an integrated UI by:
enabling a display of a first selectable control that, when selected, operates to display a demographics UI display as part of the integrated UI;
in response to selection of the first selectable control of the integrated UI, displaying the demographics UI display with data provided by a first workflow engine comprising a demographic information verification engine, wherein the demographics UI display displays alerts with patient data that differs from the demographic data stored in one or more third party data sources and marks conflicting demographic data provided by the one or more third party data sources;
enabling a display of a second selectable control that, when selected, accesses a selectable coverage UI display;
in response to selection of the second selectable control of the integrated UI, displaying the coverage UI display with data provided by a second workflow engine comprising a coverage information verification engine, wherein the coverage UI display displays coverage verification alerts for coverage issues identified between the patient data and coverage information received from the one or more third party data sources;

enabling a display of a third selectable control that, when selected, operates to display an alert overview UI display as part of the integrated UI; and in response to selection of the third selectable control of the integrated UI, displaying the alert overview UI display with alert data provided by a third workflow engine comprising an alerts engine including an alert status UI display that displays resolved and/or unresolved alerts with alert details that include a type of alert, a current alert status, and an alert category, wherein the demographic information verification engine outputs the data for the demographics UI display of the integrated UI after cross-matching the patient data with the demographic data stored in one or more data third party sources to determine if any demographic data is missing from the patient data and that the demographic data in the patient data is consistent with the demographic data stored in the one or more third party data sources, the coverage information verification engine outputs the data for the coverage UI display of the integrated UI after performing a query for coverages claimed by a patient or guarantor corresponding with the patient data and after cross-matching the patient data with the insurance coverage data stored in the one or more third party data sources to determine if the coverage data is missing from the patient data and that the coverage data in the patient data is consistent with the coverage data stored in the one or more third party data sources, and the alerts engine outputs the alert data for the alert overview UI display and one or more of the demographics UI display and the coverage UI display and generates one or more displayable alerts for display in the alert overview UI display and in one or more of the demographics UI display and the coverage UI display corresponding to the alert data affecting one or more downstream patient access workflow processes that depend on accurate data.

15. The computer readable medium of claim 14, further to:

provide access to:

the demographic information verification engine;

the coverage information verification engine;

a medical necessity validation engine;

a pre-certification engine;

an estimate engine;

a financial clearance engine; and a collections engine.

16. The computer readable medium of claim 14, further to:

receive, via the integrated UI, input in response to an alert;

determine if the input resolves the alert; and if the input resolves the alert:

update an alert status for the alert; and store the input and updated alert status in a data store.

* * * * *